United States Patent
Shirakawa et al.

(12) 
(10) Patent No.: US 6,950,710 B2
(45) Date of Patent: Sep. 27, 2005

(54) IMPLANTABLE ELECTRODE LEAD AND IMPLANTABLE MEDICAL INSTRUMENT USING THE IMPLANTABLE ELECTRODE LEAD

(75) Inventors: Katsuhiro Shirakawa, Shizuoka (JP); Yoshizo Ishizuka, Kanagawa (JP); Fuminori Tsuboi, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 306 days.

(21) Appl. No.: 09/937,062

(22) PCT Filed: Mar. 6, 2001

(86) PCT No.: PCT/JP01/01718

§ 371 (c)(1),
(2), (4) Date: Jan. 29, 2002

(87) PCT Pub. No.: WO01/66181

PCT Pub. Date: Sep. 13, 2001

(65) Prior Publication Data

US 2003/0088302 A1 May 8, 2003

(30) Foreign Application Priority Data

Mar. 6, 2000 (JP) .................................... 2000-060668

(51) Int. Cl.[7] .............................................. A61N 1/00
(52) U.S. Cl. ..................................................... 607/122
(58) Field of Search .................. 607/116, 122, 607/119, 63, 27, 28; 439/909; 600/377, 547

(56) References Cited

U.S. PATENT DOCUMENTS

| 4,922,927 | A |   | 5/1990  | Fine et al. |
|-----------|---|---|---------|-------------|
| 5,179,947 | A |   | 1/1993  | Meyerson et al. |
| 5,261,418 | A | * | 11/1993 | Ferek-Petric ................. 607/126 |
| 6,285,910 | B1| * | 9/2001  | Verness et al. ............. 607/122 |
| 6,289,250 | B1|   | 9/2001  | Tsuboi et al. |

FOREIGN PATENT DOCUMENTS

| EP | 0 813 890 A2 | 12/1997 |
| EP | 1 005 879 A1 | 6/2000 |
| JP | 11-333000 A  | 12/1999 |
| WO | 99/61098 A1  | 2/1999 |

* cited by examiner

*Primary Examiner*—Mark Bockelman
(74) *Attorney, Agent, or Firm*—Burns, Doane, Swecker & Mathis, L.L.P.

(57) ABSTRACT

An electrode lead, which is used as an implantable electrode lead and a symptom of disconnection of which can be found and detected at an early stage before complete disconnection. Also, an implantable medical instrument which uses this electrode lead safely is provided. More specifically, in an implantable electrode lead obtained by connecting conductor wires 23 and 27 with large electrical resistances and conductor wires 20 and 26 with small electrical resistances parallel to each other, when one of the low-strength conductor wires 20 and 26 is disconnected, a change in electrical resistance of the implantable electrode lead can be detected and informed. Hence, a symptom before total disconnection of the implantable electrode lead can be detected.

15 Claims, 15 Drawing Sheets

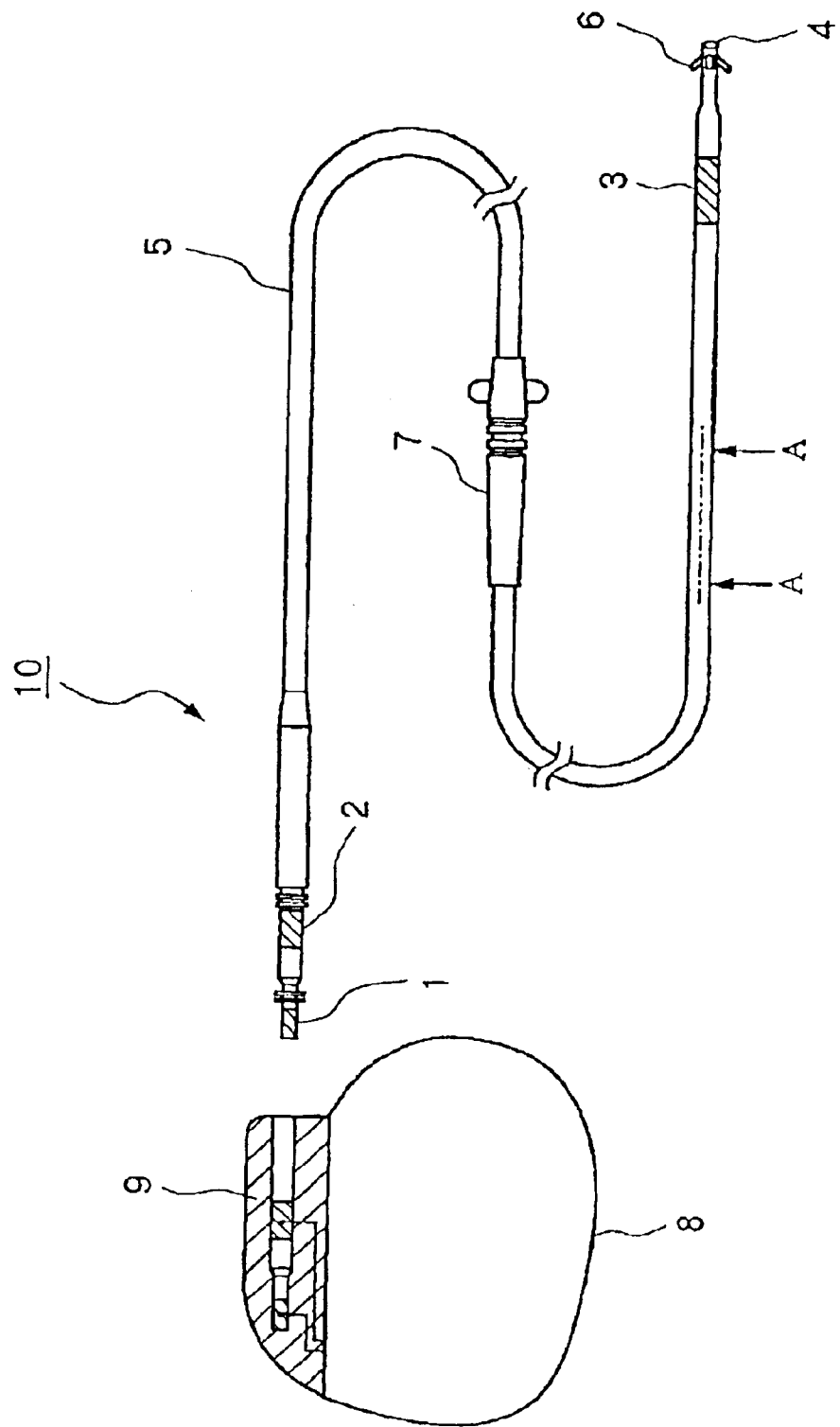

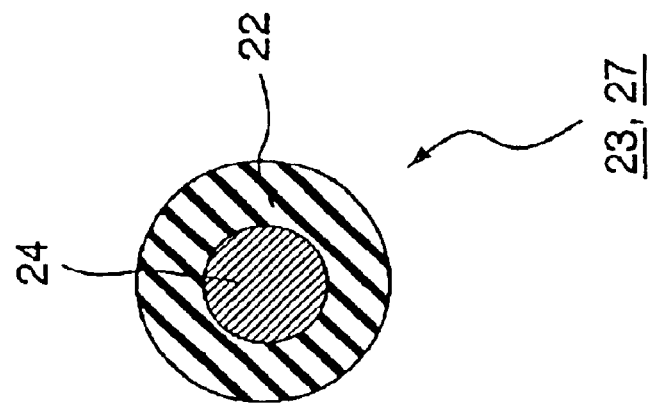
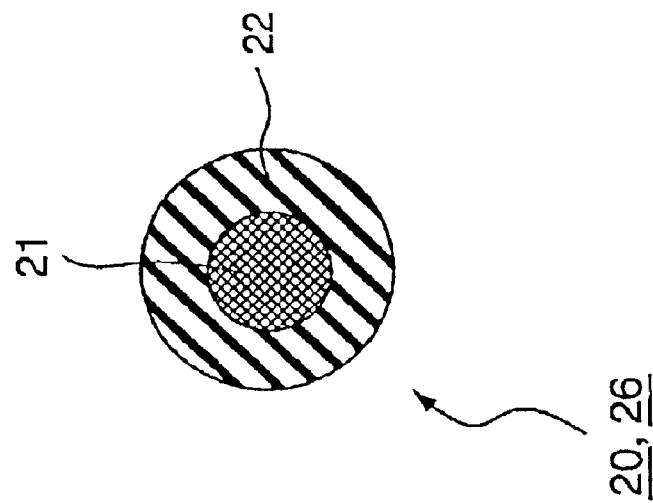

FIG. 5

| | |
|---|---|
| LENGTH OF CONDUCTOR COIL | 550 mm |
| NUMBER OF TURNS OF CONDUCTOR COILS | FOUR (TWO ON TIP ELECTRODE SIDE, TWO ON RING ELECTRODE SIDE) |
| DIAMETER OF CONDUCTOR COIL (AVERAGE DIAMETER) | 0.9 mm |
| DIAMETER OF CONDUCTOR WIRE | 0.1 mm |
| THICKNESS OF INSULATING COATING | 0.05 mm |
| RESISTANCE OF CONDUCTOR WIRE (SILVER) | 4.06 Ω |
| RESISTANCE OF CONDUCTOR WIRE (COBALT ALLOY) | 258.55 Ω |
| RESISTANCE OF LIVING BODY | 1000 Ω |

FIG. 6A

| RESISTANCE | TIP ELECTRODE-SIDE LEAD RESISTANCE (Ω) | LIVING BODY RESISTANCE (Ω) | RING ELECTRODE-SIDE LEAD RESISTANCE (Ω) |
|---|---|---|---|
| BEFORE DISCONNECTION | 4.06 | 1000 | 4.06 |
| AFTER DISCONNECTION | 258.55 (DISCONNECTION) | 1000 | 4.06 |

FIG. 6B

| RESISTANCE | TOTAL RESISTANCE BEFORE DISCONNECTION (Ω) | TOTAL RESISTANCE AFTER DISCONNECTION (Ω) | RATIO OF TOTAL RESISTANCE (AFTER DISCONNECTION / BEFORE DISCONNECTION) (-) |
|---|---|---|---|
| FIRST EMBODIMENT | 1008.13 | 1262.61 | 1.25 |

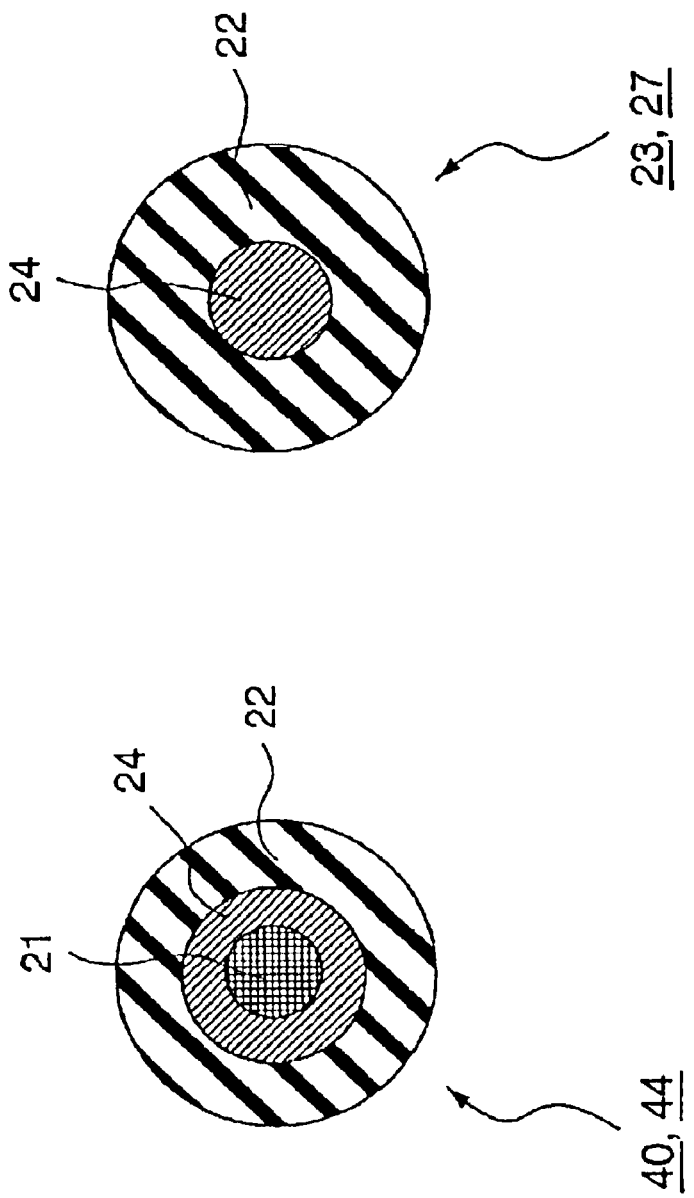

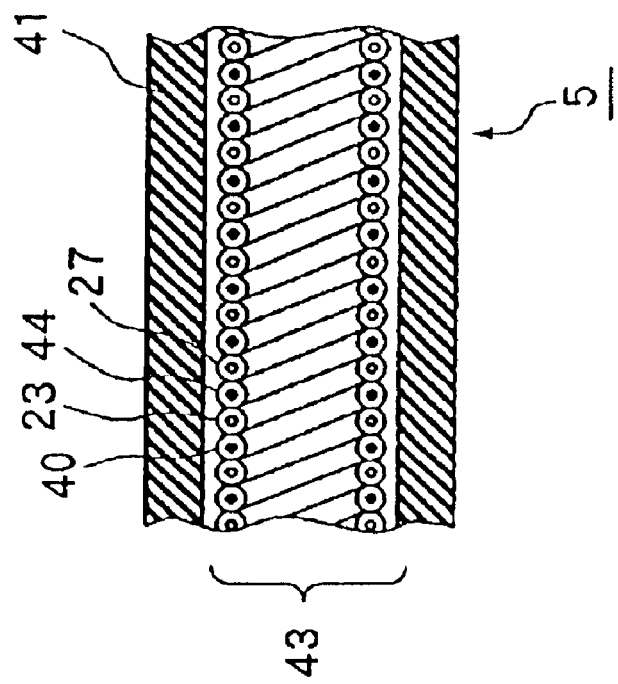
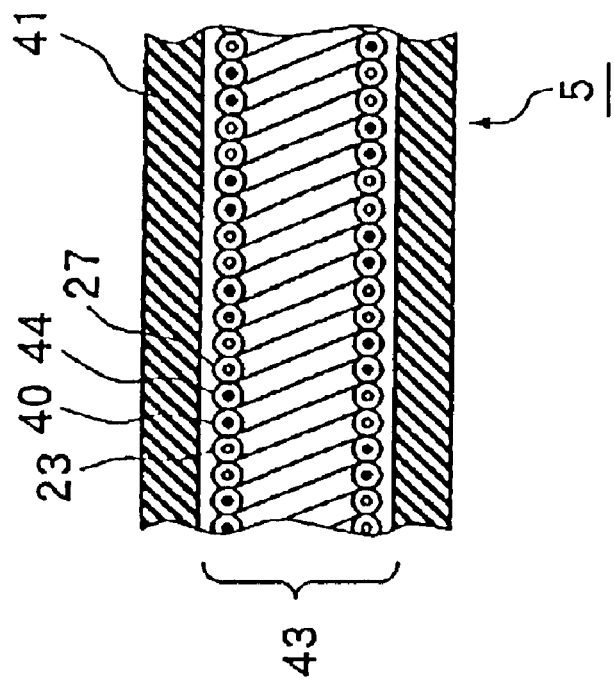

F I G. 10A

| RESISTANCE | CHIP ELECTRODE-SIDE LEAD RESISTANCE (Ω) | LIVING BODY RESISTANCE (Ω) | RING ELECTRODE-SIDE LEAD RESISTANCE (Ω) |
|---|---|---|---|
| BEFORE DISCONNECTION | 14.85 | 1000 | 14.85 |
| AFTER DISCONNECTION | 258.55 (DISCONNECTION) | 1000 | 14.85 |

F I G. 10B

| RESISTANCE | TOTAL RESISTANCE BEFORE DISCONNECTION (Ω) | TOTAL RESISTANCE AFTER DISCONNECTION (Ω) | RATIO OF TOTAL RESISTANCE (AFTER DISCONNECTION / BEFORE DISCONNECTION) (-) |
|---|---|---|---|
| SECOND EMBODIMENT | 1029.70 | 1273.40 | 1.24 |

FIG. 15A

| RESISTANCE | CHIP ELECTRODE-SIDE LEAD RESISTANCE (Ω) | LIVING BODY RESISTANCE (Ω) | RING ELECTRODE-SIDE LEAD RESISTANCE (Ω) |
|---|---|---|---|
| BEFORE DISCONNECTION | 7.88 | 1000 | 7.88 |
| AFTER DISCONNECTION | 15.76 (DISCONNECTION) | 1000 | 7.88 |

FIG. 15B

| TOTAL RESISTANCE BEFORE DISCONNECTION (Ω) | TOTAL RESISTANCE AFTER DISCONNECTION (Ω) | RATIO OF TOTAL RESISTANCE (AFTER DISCONNECTION / BEFORE DISCONNECTION) (-) |
|---|---|---|
| 1015.76 | 1023.63 | 1.008 |

IMPLANTABLE ELECTRODE LEAD AND IMPLANTABLE MEDICAL INSTRUMENT USING THE IMPLANTABLE ELECTRODE LEAD

TECHNICAL FIELD

The present invention relates to an implantable electrode lead used together with an implantable heart pacemaker or implantable defibrillator, and an implantable medical instrument using the implantable electrode lead.

BACKGROUND ART

Many types of conventional electrode leads implantable in living bodies (to be referred to as implantable electrode leads hereinafter) which are used together with implantable heart pacemakers or implantable defibrillators, are known.

An implantable electrode lead is generally comprised of an electrode for supplying an electrical stimulation pulse to the heart or sensing an electrically evoked response of the heart, an electrical connector connected to a heart pacemaker (or defibrillator), and a lead body made up of an electrical conductor wire for connecting the electrode and electrical connector to each other and transmitting an electrical signal between the electrode and heart pacemaker (or defibrillator) and an electrical insulation covering the electrical conductor wire.

In the implantable electrode lead, the electrode and part of the lead body are inserted in the heart and vein, while the remaining lead body and the electrical connector are placed outside the vein and connected to the connection housing of the heart pacemaker or implantable defibrillator.

As an example of a lead body for an implantable electrode lead, a bipolar type lead body in which a plurality of insulation-coated conductor are connected parallel to each other is used, as shown in Japanese Patent Laid-Open No. 11-333000. The conductor wires are wound parallel to each other insulated from each other so as to form a coil, and the conductor wires are covered with a sheath, thus forming a lead body.

According to another general lead body, one with a coaxial structure is available, which is comprised of two types of conductor coils with different average diameters, an insulating sheath located between the conductor coils, and a sheath located at the outermost surface of the lead body.

A bipolar type implantable electrode lead body comprised of a plurality of conductor wires with respect to one electrode is used because, even if one of the conductor wires is disconnected, as long as the remaining conductor wires are connected normally, an electrical signal from the heart pacemaker can be continuously transmitted to the living tissue.

As the implantable electrode lead, one with a small energy loss in the conductor wires is sought. For this reason, two conductor wires with the same low resistance are used.

In a conventional implantable electrode lead using two low-resistance conductor wires, even if one conductor wire is disconnected, this produces a small change in electrical resistance, as will be described later. Therefore, it is rather difficult to externally detect disconnection from a change in electrical resistance after the implantable electrode lead is implanted in the living body.

This will be described in detail with reference to FIGS. 14 and 15.

FIG. 14 shows a case in which a bipolar type implantable electrode lead, comprised of two low-resistance conductor wires connected parallel with each other, is connected to a living tissue. The lead body of an implantable electrode lead 60 is comprised of two portions, i.e., a tip electrode-side lead resistor 61 and ring electrode-side lead resistor 62. The implantable electrode lead 60 and the living tissue 32 are connected to each other through a tip electrode 4 and ring electrode 3, and the living tissue 32 and the implantable electrode lead 60 substantially electrically form a series circuit as shown in FIG. 14. The implantable electrode lead 60 is connected to an implantable heart pacemaker through a connector pin 1 and connector ring 2.

Each of the tip electrode-side lead resistor 61 and ring electrode-side lead resistor 62 is comprised of two conductor wires with the same resistance (R1). To obtain the resistance R1 used for the implantable heart pacemaker, for example, a low-resistance conductor wire with approximately 16 Ω is used. A bioelectrical resistance 32 (R4) of the living tissue is approximately 1,000 Ω.

FIGS. 15A and 15B show a case wherein changes in resistance that occur when, of the four conductor wires, one conductor-wire of the tip electrode-side lead resistor 61 is disconnected with the condition described above are obtained. FIG. 15A shows changes in electrical resistance upon disconnection. The resistance of the tip electrode-side lead resistor 61 increases from 7.88 Ω to 15.76 Ω upon disconnection.

FIG. 15B shows a change in total electrical resistance obtained on the basis of FIG. 15A. Although the total electrical resistance after disconnection (1,023.63 Ω) is slightly larger than that (1,015.76 Ω) obtained before disconnection, the increase is small, approximately 1% (the ratio of total electrical resistance before disconnection to that after disconnection: 1.008). Also, since the bioelectical resistance sometimes fluctuates by approximately several 10 Ω, it is difficult to determine disconnection from the 1% increase in resistance.

As another lead body for the bipolar type implantable electrode lead, one with a coaxial structure is also available, which is comprised of two types of conductor coils with different average diameters, an insulating sheath located between the conductor coils, and a sheath located at the outermost surface of the lead body.

When the conductor wires of the same pole are not insulated from each other, as in the conventional coaxial structure, the adjacent conductor wires are largely influenced by the contact resistance. As the contact resistance varies depending on the movement or deformation of the lead in the living body, it is sometimes difficult to externally detect the contact resistance from a change in resistance.

When, however, an implantable electrode lead used in a heart pacemaker or implantable defibrillator is completely disconnected, the treatment necessary for the patient cannot be performed, sometimes leading to the worst result such as death of the patient. For this reason, it is desired that a symptom of disconnection of the implantable electrode lead be found at an early stage before complete disconnection.

DISCLOSURE OF INVENTION

The present invention has been made in view of the above problems of the prior art, and has as its object to provide an implantable electrode lead with a bipolar type insulated parallel-wire coil structure, in which electrical resistance can be kept low, and when one of a plurality of conductor wires arranged for one electrode is disconnected, a change in electrical resistance generated by disconnection is detected without being influenced by a contact resistance, so that the symptom of disconnection of the implantable electrode lead can be detected at an early stage before complete disconnection.

It is another object of the present invention to provide an implantable medical instrument that uses this implantable electrode lead and can be used more safely.

In order to achieve the above objects, the implantable electrode lead according to the present invention has the following structure.

More specifically, there is provided an implantable electrode lead having a distal end provided with at least one electrode to be implanted in a predetermined portion of a living body in order to perform at least one of transmission of an electrical stimulation pulse to a living body and sensing of an electrical signal from the living body, a proximal end provided with connecting means to be connected to an implantable medical instrument, and a lead body provided between the distal end and the proximal end and adapted to electrically connect the electrode and the connecting means to each other, characterized in that the lead body includes a plurality of wires with different mechanical characteristics and insulated from each other, the plurality of wires being electrically connected to the at least one electrode to be parallel to each other.

Preferably, the plurality of wires are wires with different electrical resistances.

Preferably, each of the wires has a single layer made of at least one metal material or alloy material, or a composite wire with a plurality of different single layers made of at least one metal material or alloy material.

Preferably, the composite wire with the plurality of different single layers has a cladding structure obtained by stacking a plurality of types of single layers made of different types of metal materials or alloy materials, or by covering a first single layer among the plurality of types of single layers with a second single layer among the plurality of types of single layers.

Preferably, the plurality of wires are structured by using different materials.

Preferably, among the plurality of wires, a first wire has an electrical resistivity of not more than 5 $\mu\Omega\cdot$cm and a second wire has an electrical resistivity of not less than 5 $\mu\Omega\cdot$cm.

Preferably, the composite wire has a first single layer made of a metal material or alloy material with an electrical resistivity of not more than 5 $\mu\Omega\cdot$cm and a second single layer made of a metal material or alloy material with an electrical resistivity of not less than 5 $\mu\Omega\cdot$cm.

Preferably, the first and second single layers of the composite wire contain silver and a cobalt alloy, respectively.

Preferably, the lead body comprises a helical parallel coil of the plurality of wires insulated from each other.

In order to achieve the above objects, an implantable medical instrument according to the present invention has the following arrangements.

More specifically, there is provided an implantable medical instrument using an implantable electrode lead having an electrode to be implanted in a predetermined portion and a lead body electrically connected to the electrode, wherein the lead body includes a plurality of wires with different mechanical characteristics and insulated from each other, the plurality of wires being electrically connected to the at least one electrode parallel to each other, and the implantable medical instrument has informing means for discriminating and informing that at least one of the different wires is fractured.

Preferably, the implantable medical instrument further has measuring means for measuring a motion state or posture of the living body where the electrode is implanted.

Preferably, the informing means measures a parameter that changes on the basis of a change in total electrical resistance of the plurality of wires, compares the parameter with a preset reference parameter, and informs that at least one of the plurality of wires is fractured when the parameter that changes is smaller than the reference parameter.

Preferably, the parameter includes either one of current, frequency, and time.

Preferably, the measuring means further has acceleration sensor means for measuring an acceleration, and measures the motion state or posture of the living body on the basis of a measurement result of the acceleration sensor means.

Preferably, the implantable medical instrument further has storage means, and when a measurement result obtained by the measuring means satisfies a predetermined condition, the measurement result is recorded in the storage means.

Preferably, the lead body comprises a helical parallel coil of the plurality of wires insulated from each other.

BRIEF DESCRIPTION OF DRAWINGS

FIG. 1 is a view showing an example of an implantable electrode lead and an implantable instrument using the same;

FIG. 2A is a sectional view of a low-resistance conductor wire;

FIG. 2B is a sectional view of a high-resistance conductor wire;

FIG. 5 is a table showing the sizes and characteristics of conductor wires and a conductor coil;

FIG. 6A is a table showing electrical resistances before and after disconnection when the implantable electrode lead is connected to the living body;

FIG. 6B is a table showing a change in total electrical resistance upon disconnection when the implantable electrode lead is connected to the living body;

FIG. 7A is a sectional view of a low-resistance conductor wire;

FIG. 7B is a sectional view of a high-resistance conductor wire;

FIG. 9A is a sectional view of an implantable electrode lead;

FIG. 9B is a sectional view of an implantable electrode lead with another arrangement;

FIG. 10A is a table showing electrical resistances before and after disconnection when the implantable electrode lead is connected to the living body;

FIG. 10B is a table showing a change between a total electrical resistance before disconnection and that after disconnection when an implantable electrode lead is connected to the living body;

FIG. 15A is prior art data showing electrical resistances before and after disconnection when the conventional implantable electrode lead is connected to the living body; and FIG. 15B is prior art data showing a change in total electrical resistance upon disconnection when the conventional implantable electrode lead is connected to the living body.

BEST MODE FOR CARRYING OUT THE INVENTION

Figure 3:
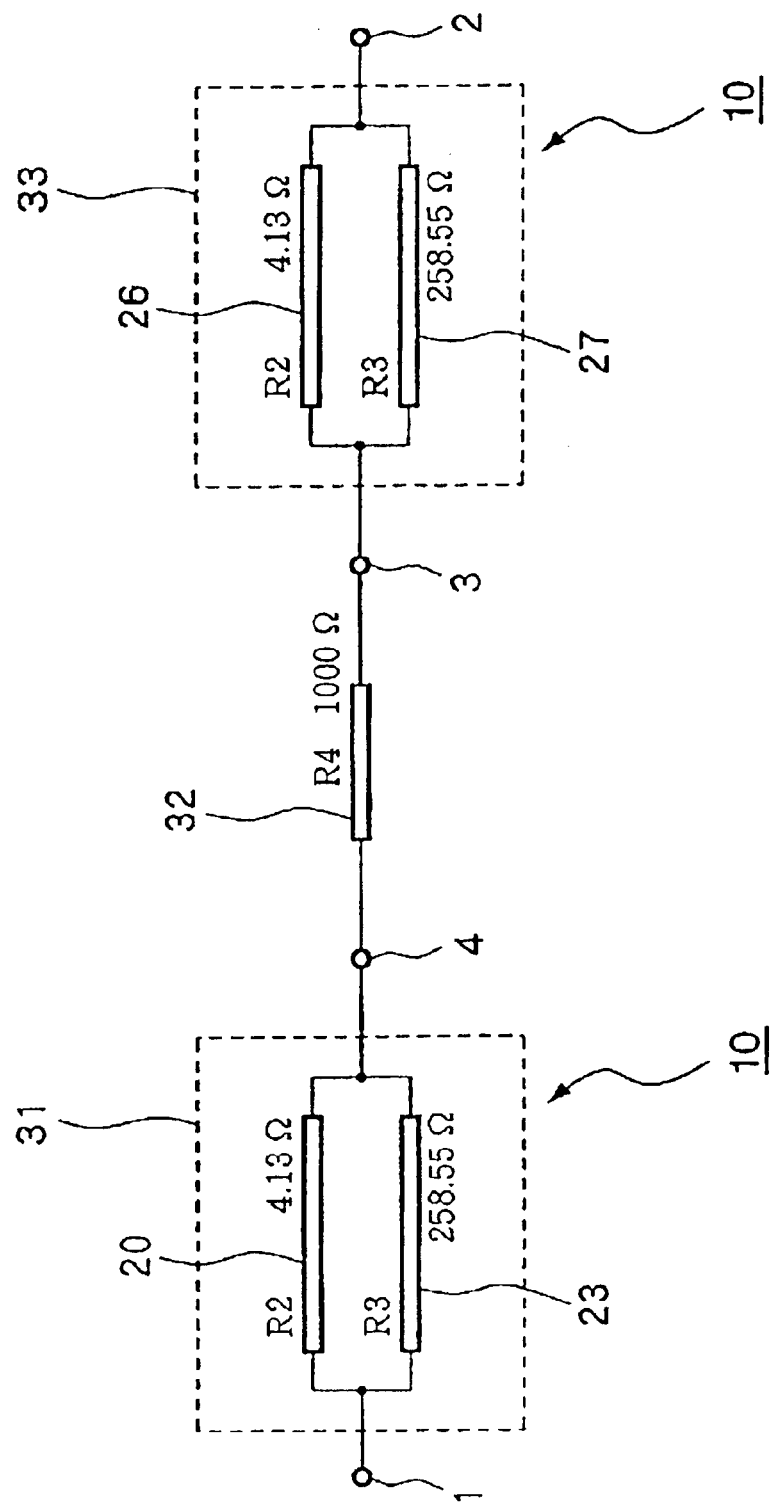
FIG. 3 is a circuit diagram obtained when an implantable electrode lead is connected to the living body.

The preferred embodiments of the present invention will be exemplified in detail with reference to the accompanying drawings. Note that the scope of the present invention is not limited to the relative positions, numerical values, and the like of the constituent elements described in the embodiments unless otherwise specified.

[First Embodiment]

[Overall Arrangement of Heart Pacemaker and Implantable Electrode Lead]

FIG. 1 is a view showing a bipolar type implantable electrode lead 10 as an implantable electrode lead according to the first embodiment of the present invention, and a heart pacemaker 8 as an example of an implantable instrument using it.

Referring to FIG. 1, the implantable electrode lead 10 has a tip electrode 4 at its distal end implanted in the heart and a ring electrode 3 on its outer surface near the tip electrode 4, and a connector pin 1 at its proximal end to be connected to the heart pacemaker 8 and a connector ring 2 on its outer surface near the connector pin 1, and is formed of a predetermined-length flexible lead body 5 that electrically connects these components to each other.

The tip electrode 4 is electrically connected to the connector pin 1, and the ring electrode 3 is electrically connected to the connector ring 2. The connector pin 1 and connector ring 2 are mechanically and electrically detachably connected to a connector cavity 9 for the heart pacemaker 8 or an implantable defibrillator (not shown).

An endocardium fixing portion 6, having such a shape that it is caught by a trabeculae carneae or chorda in the heart cavity so as to fix the implantable electrode lead 10 to an endocardium, thereby setting the implantable electrode lead 10 immobile, is provided near the tip electrode 4.

A sleeve 7 serves to protect the lead body 5 when the lead body 5 is fixed to the living tissue near a vein inserting portion, and is mounted on the outer surface of the lead body 5 so as to be movable in the longitudinal direction of the lead body 5. The lead body 5 is fixed as it is sutured together with the outer surface of the sleeve 7 to the living tissue.

[Bipolar Type Implantable Electrode Lead]

A conductor coil and conductor wires that make up the lead body 5 will be described with reference to FIGS. 2 to 4.

Figure 4A:
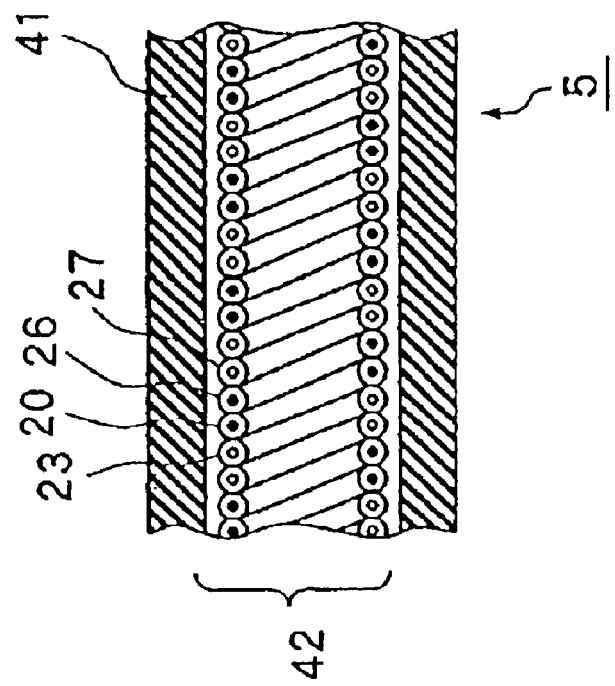
FIG. 4A is a sectional view of an implantable electrode lead.
Figure 4B:
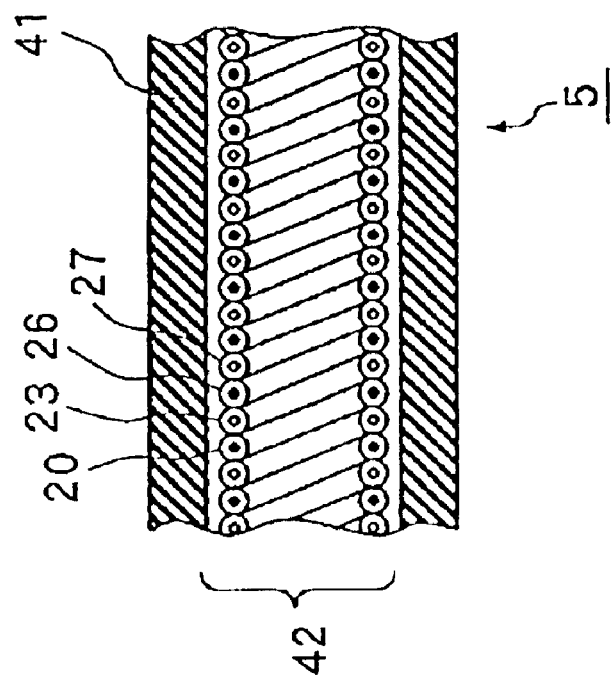
FIG. 4B is a sectional view of an implantable electrode lead with another arrangement.

FIGS. 4A and 4B are each a sectional view of a portion indicated by arrows A—A of the lead body 5 in FIG. 1, and show a case wherein two low-resistance conductor wires 20 and 26 and two high-resistance conductor wires 23 and 27 are arranged in different manners.

The lead body 5 is made up of a conductor coil 42 with an insulated four-parallel-wire structure obtained by helically winding the insulation-coated conductor wires 20, 23, 26, and 27, and an insulating sheath 41 for insulating and covering the conductor coil 42. The lead body 5 is narrow in order to reduce the compression force repeatedly received between the clavic and first rib.

The conductor coil 42 is formed of four conductor wires, two of which are the low-resistance conductor wires 20 and 26 with small electrical resistances shown in FIG. 2A, and the remaining two of which are the high-resistance conductor wires 23 and 27 with large electrical resistances shown in FIG. 2B. These four conductor wires make up the insulated four-parallel-wire structure shown in FIGS. 4A and 4B, so the internal stress acting on the respective conductor wires, when the lead body 5 deforms, is reduced.

Of the four conductor wires, two (a low- and a high-resistance conductor wires 20 and 23) are connected parallel to each other between the connector pin 1 and tip electrode 4, as shown in FIG. 3, to form a tip electrode-side lead resistor 31, while the remaining two (a low- and a high-resistance conductor wires 26 and 27) are connected parallel to each other between the connector ring 2 and ring electrode 3, to form a ring electrode-side lead resistor 33.

The two low-resistance conductor wires 20 and 26 and the two high-resistance conductor wires 23 and 27 can have either one of the arrangements shown in FIGS. 4A and 4B.

The low-resistance conductor wires 20 and 26 and the high-resistance conductor wires 23 and 27 will be described with reference to FIGS. 2A and 2B. The first layer (cladding) of each of the low-resistance conductor wires 20 and 26 is an insulation coat for insulating the core from the outside, and is made of a fluoroplastic material. The second layer (core) serves to transmit an electrical signal, and is made of a material with a low electrical resistivity (second metal material 21), e.g., silver or copper. In this embodiment, silver is used.

The first layer (cladding) of each of the high-resistance conductor wires 23 and 27 is also formed of an insulation coat made of a fluoroplastic material in order to insulate the core from the outside. The second layer (core) serves to transmit an electrical signal and is made of a material with a lower electrical resistivity (second metal material 24), e.g., stainless steel or a cobalt-group alloy. In this embodiment, MP35N as a cobalt-group alloy with excellent corrosion resistance and mechanical characteristics is used.

A case will be described in which the bipolar type implantable electrode lead 10 formed by connecting two low-resistance conductor wires parallel to each other is connected to the living tissue and an implantable heart pacemaker.

The lead body of the implantable electrode lead 10 is formed of two portions, i.e., the tip electrode-side lead resistor 31 and ring electrode-side lead resistor 33. The implantable electrode lead 10 and the living tissue are connected to each other through the tip electrode 4 and ring electrode 3, and the living tissue and the implantable electrode lead 10 substantially electrically form a series circuit as shown in FIG. 3. The implantable electrode lead 10 is connected to an implantable heart pacemaker through the connector pin 1 and connector ring 2.

The tip electrode-side lead resistor 31 is comprised of the low- and high-resistance conductor wires 20 and 23, and the ring electrode-side lead resistor 33 is comprised of the low- and high-resistance conductor wires 26 and 27. In this embodiment, as shown in FIG. 5, the coil using the low- and high-resistance conductor wires 20 and 23 has a length of 550 mm. The resistances are 4.06 Ω and 258.55 Ω respectively. The bioelectrical resistance 32 of the living tissue is approximately 1,000 Ω.

[Mechanical Strength of Implantable Electrode Lead]

Assume that, while the implantable electrode lead 10 is attached to the living tissue, a tensile stress repeatedly acts on the implantable electrode lead 10, so one of the four conductor wires making up the implantable electrode lead 10 is disconnected. The tensile strength of each of the low-resistance conductor wires 20 and 26 is 290 MPa, and that of each of the high-resistance conductor wires 23 and 27 is 520 MPa.

With these conditions, when a tensile stress repeatedly acts on the implantable electrode lead 10, either one of the two low-resistance conductor wires 20 and 26 is supposed to fracture first.

[Change in Total Electrical Resistance Upon Fracture of Low-Resistance Conductor Wire]

A case will be described wherein a change in electrical resistance that occurs when the low-resistance conductor wire 20 fractures under the conditions of FIG. 3 is obtained.

The total electrical resistance (Ω) formed of the implantable electrode lead 10 and the living tissue is given by the following equation (1):

$$\text{Total Electrical Resistance} = \text{Tip Electrode-Side Lead Resistance} + \text{Bioelectrical Resistance} + \text{Ring Electrode-Side Lead Resistance} \quad (1)$$

Assume that the bioelectrical resistance is 1,000 Ω and that the tip electrode-side lead resistance or electrode-side ring lead resistance is only the resistance of a conductor coil formed of two wires parallel to each other, as shown in FIG. 3. The resistances in the electrode and connecting portions are negligible.

FIGS. 6A and 6B show results of changes in resistance which are obtained by using equation (1) when the low-resistance conductor wire 20 of the tip electrode-side lead resistor 31 is disconnected with the conditions of FIG. 5.

FIG. 6A shows a change in resistance upon disconnection of the respective portion. The resistance of the tip electrode-side lead resistor 61 increases from 4.06 Ω to 258.55 Ω. As a result, as shown in FIG. 6B, the total electrical resistance increases from 1,008.13 Ω to 1,262.61 Ω. The resistance increases by 25% due to disconnection (the ratio of total electrical resistance before disconnection to that after disconnection: 1.25).

This result is compared against the prior art disconnect condition shown in FIGS. 15A and 15B described above. When two identical low-resistance conductor wires are used (FIGS. 15A and 15B), the increase in resistance is 1%. When conductor wires with different resistances are used, as in this embodiment (FIGS. 6A and 6B), the resistance after disconnection can be larger than that before disconnection by up to 25%. Therefore, even if the bioelectrical resistance slightly changes, disconnection of one low-resistance conductor wire can be determined by measuring the resistances before and after disconnection.

When the total electrical resistance (1,008.13 Ω) before disconnection of this embodiment is compared with the conventional total electrical resistance (1,015.76 Ω) obtained with low-resistance conductor wires, it decreases by only 1%. Thus, the implantable electrode lead 10 according to this embodiment can maintain a low resistance of almost the conventional level.

When a fracture that greatly increases the electrical resistance, although not leading to disconnection, occurs in one of the plurality of conductor wires of the conductor wires, the symptom of disconnection of the implantable electrode lead can be detected.

In the case described above, this embodiment is applied to measurement of a resistance between the connector pin 1 and connector ring 2, that is, in the bipolar mode. It is readily understood that the same effect can be obtained in measurement of a resistance between the ring electrode 3 or tip electrode 4 and another reference point, e.g., the main body case of the heart pacemaker, i.e., in the unipolar mode.

[Second Embodiment]

An implantable electrode lead 11 according to the second embodiment of the present invention will be described with reference to FIGS. 7 to 10.

The second embodiment is different from the implantable electrode lead 10 of the first embodiment in only low-resistant conductor wires 40 and 44 used in a conductor coil 43 constituting the implantable electrode lead 11 shown in FIG. 7A. The arrangement, structure, operation, and the like of high-resistance conductor wires 23 and 27 and the like shown in FIG. 7B are entirely the same as those of the first embodiment. The same arrangements as in the first embodiment are denoted by the same reference numerals, and a description thereof will be omitted.

Each of the low-resistant conductor wires 40 and 44 has a three-layered structure as shown in FIG. 7A. The first layer (cladding) is an insulating film 22 fabricated from a fluoroplastic material. The second layer (first core) is fabricated from a first metal material 24 with a comparatively high electrical resistivity, e.g., stainless steel or a cobalt-group alloy, and has excellent corrosion resistance and mechanical characteristics.

The third layer (second core) is fabricated from a second metal material 21 with a low electrical resistivity, e.g., silver or copper. The second and third layers are brought into contact with each other, so the electrical resistance of the entire conductor wire is suppressed. In this embodiment, MP35N, which is a cobalt-group alloy, is used as the first metal material 24, and silver with a low electrical resistivity is used as the second metal material 21.

In this embodiment, the low-resistant conductor wire 40 with the three-layered structure shown in FIG. 7A is used because, by covering a silver wire having a low fracture strength with the cobalt-group alloy (MP35N), the silver wire is protected and defects formed in the silver surface during fabrication of the silver layer are decreased. The low-resistant conductor wire 40 has a slightly higher fracture strength than that of the low-resistance conductor wire 20, although it is lower than that of the high-resistance conductor wire 23.

As the arrangement of the conductor coil 43 using the two low-resistant conductor wires 40 and 44 and two high-resistance conductor wires 23 and 27, either one of embodiments shown in FIGS. 9A and 9B can be selected.

The arrangement formed by connecting the implantable electrode lead 11 to the living tissue is as shown in FIGS. 9A and 9B. The resistances of the low-resistant conductor wires 40 and 44 are 15 Ω in the case of this embodiment wherein the conductor coil has a length of 550 mm. Other resistances are equal to those of the first embodiment shown in FIG. 5.

[Change in Total Electrical Resistance Upon Fracture of Low-Resistance Conductor Wire]

Figure 8:
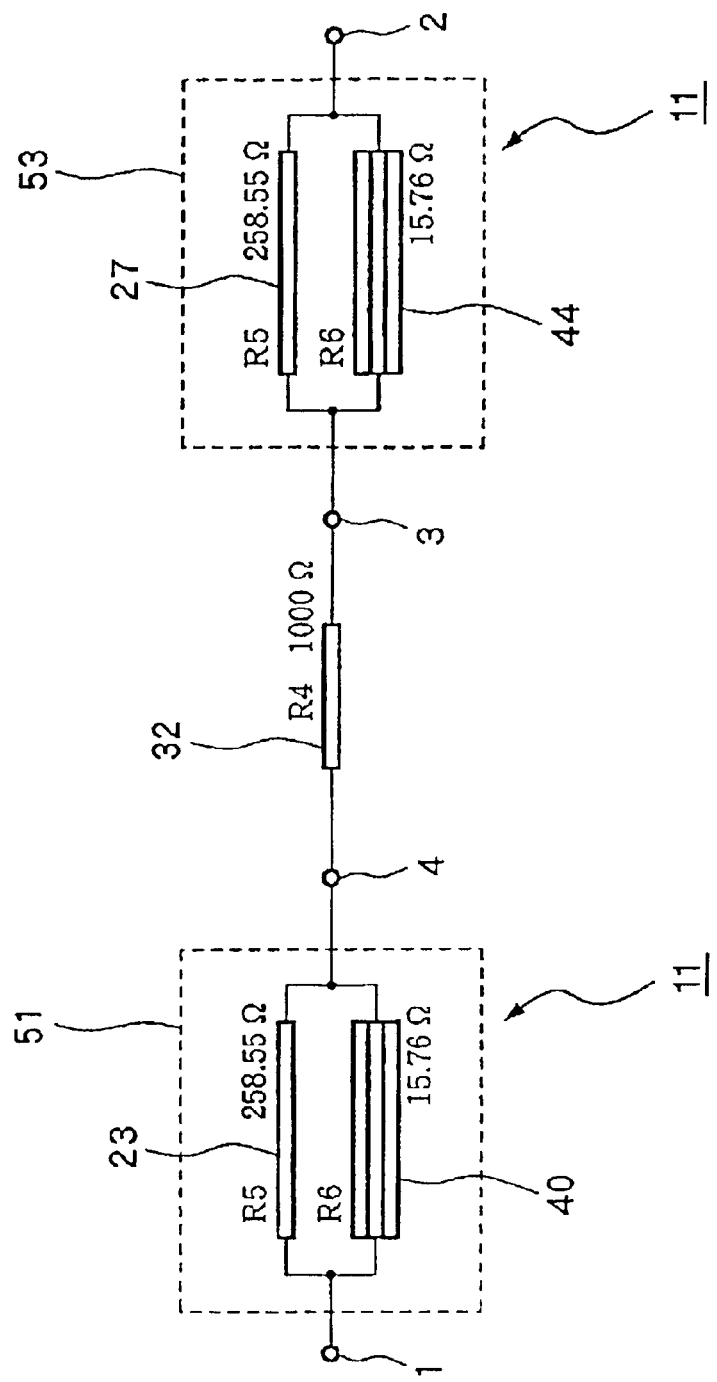
FIG. 8 is a circuit diagram obtained when an implantable electrode lead is connected to the living body.

Assume that, with the implantable electrode lead 11 being attached to the living tissue as shown in FIG. 8, a tensile stress repeatedly acts on the implantable electrode lead 11, as described above, so one of the four conductor wires constituting the implantable electrode lead 11 is accidentally fractured.

The tensile strengths of the low-resistant conductor wires 40 and 44 are lower than those of the high-resistance conductor wires 23 and 27. Hence, with the above conditions, when a tensile stress repeatedly acts on the implantable electrode lead 11, either one of the two low-resistance conductor wires 40 and 44 is supposed to fracture first.

A change in electrical resistance that occurs when the low-resistance conductor wire 40 fractures with the conditions of FIG. 8 is obtained. FIGS. 10A and 10B show the results.

FIG. 10A shows a change in resistance upon disconnection. The resistance of the tip electrode-side lead resistor 51 increases from 14.85 Ω to 258.55 Ω upon disconnection. As shown in FIG. 10B, the total electrical resistance after disconnection obtained from equation (1) is higher than that obtained before disconnection by 24%, as shown in FIG. 10B (the ratio of total electrical resistance before disconnection to that after disconnection: 1.24).

The rate of increase of the total electrical resistance after disconnection is nearly the same as the result obtained in the first embodiment (FIGS. 6A and 6B). Hence, it is apparent that in the second embodiment as well, disconnection of the low-resistant conductor wire 40 or 44 can be detected with the same detection sensitivity as that of the first embodiment.

When the total electrical resistance (1,029.70 Ω) before disconnection of this embodiment is compared with the conventional total electrical resistance (1,015.76 Ω) obtained with low-resistance conductor wires, it increases by only 1%. Thus, the implantable electrode lead 11 according to this embodiment can maintain a low resistance of almost the prior art level.

From the foregoing, with either the implantable electrode lead 10 or 11, the total electrical resistance can be suppressed low, and when one conductor wire is accidentally fractured, it can be detected with a high sensitivity.

When a fracture that greatly increases the electrical resistance, although not leading to disconnection, occurs in one of the plurality of conductor wires, a symptom of disconnection of the implantable electrode lead can be detected.

In the above embodiment, two wires connected parallel to each other are implemented by using metal materials with different electrical resistances and mechanical characteristics. However, according to the principle of the present invention, the metal materials used to form the respective wires do not necessarily have different characteristics.

Even if the two wires are made of one metal material, they can have different electrical resistances and mechanical characteristics by only changing the shapes of the wires, e.g., making one wire thinner than the other or by forming a groove in the outer surface of one wire. As a result, degradation in lead can be detected at an early stage.

(Measurement of Total Electrical Resistance)

A method of measuring the total electrical resistance will be described with reference to FIGS. 11 to 13, wherein the implantable electrode lead 11 according to the second embodiment is connected to an implantable heart pacemaker 8 so that it is implanted in the living body.

Figure 11:
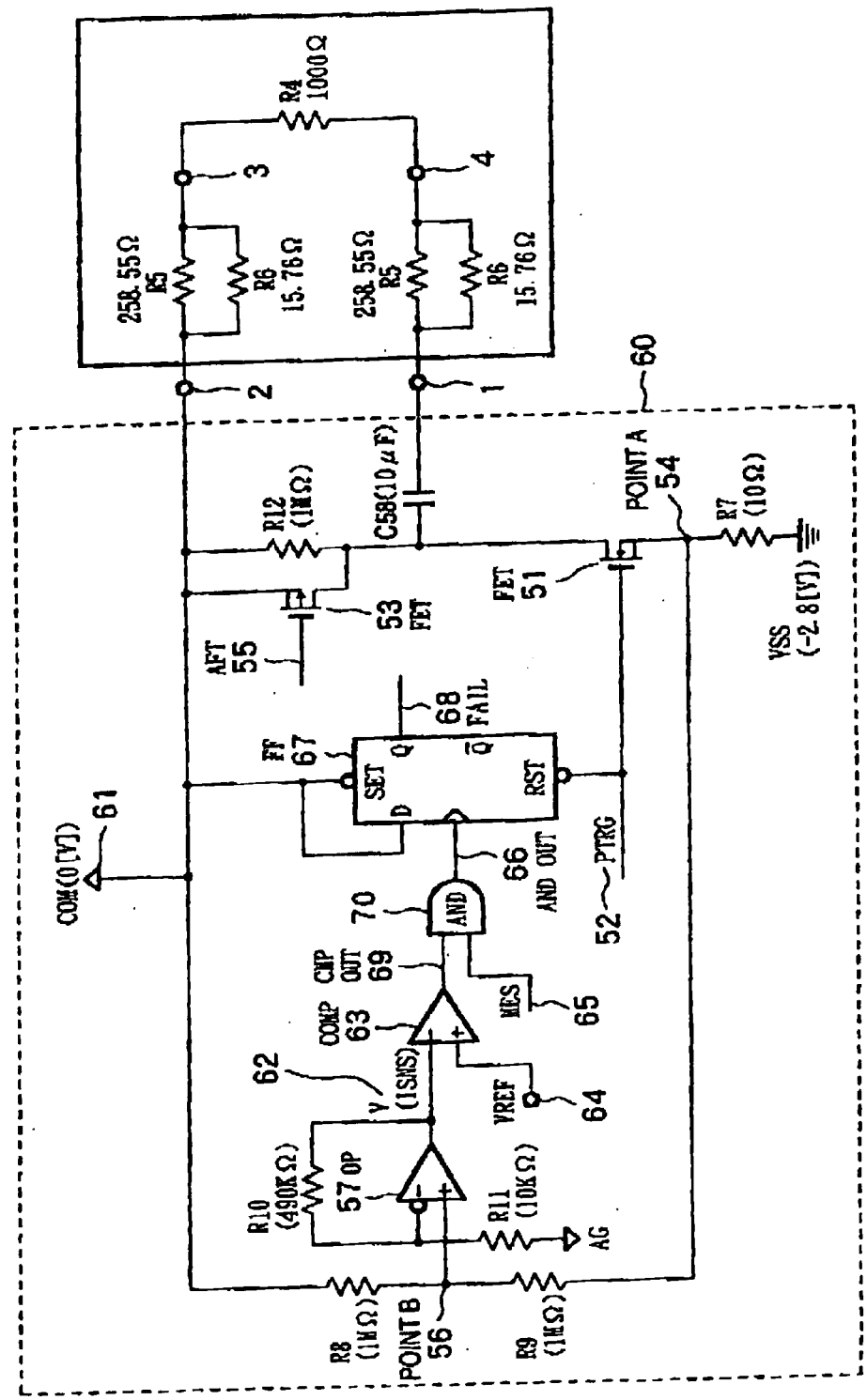
FIG. 11 shows an electrical resistance measurement unit.
Figure 12:
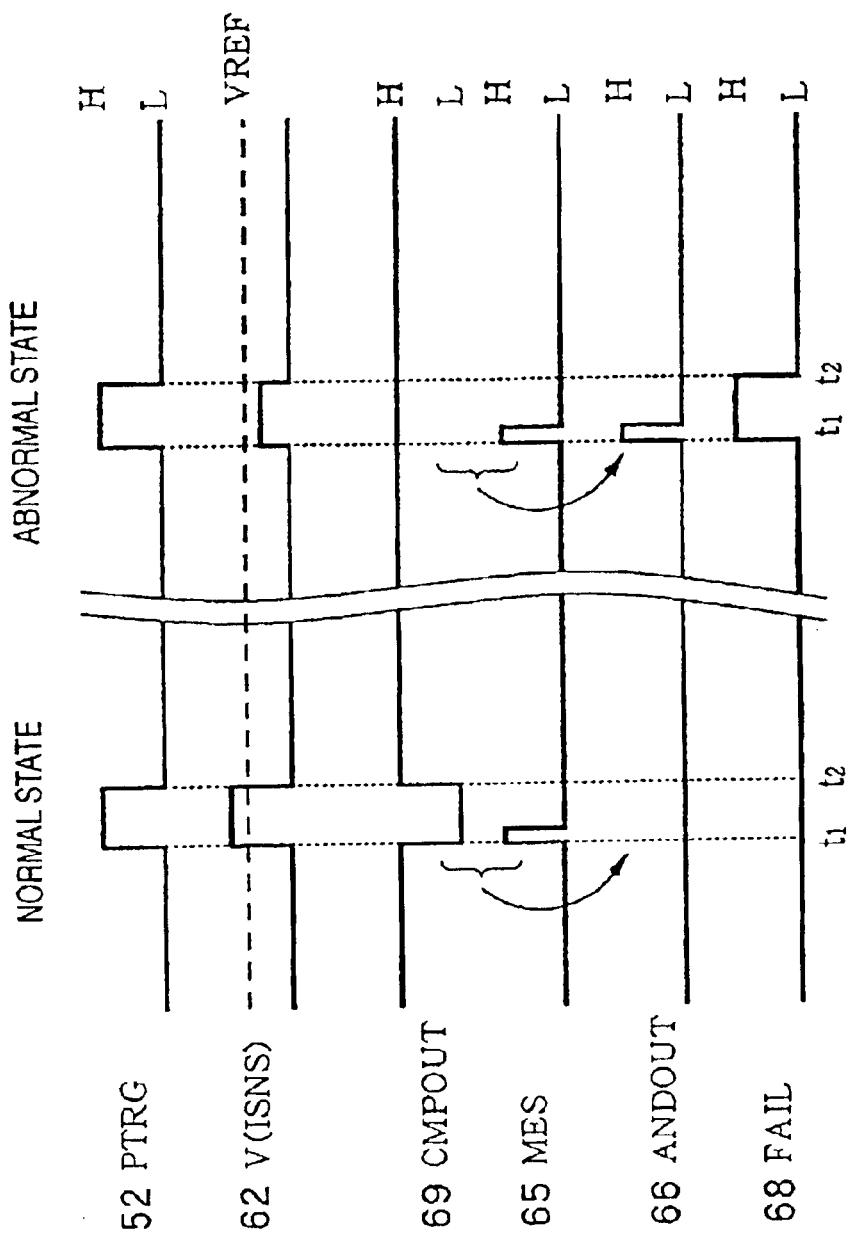
FIG. 12 is a timing chart of the respective signals.

FIG. 11 shows a practical example of an electrical resistance measurement circuit, and FIG. 12 is a timing chart of signals used in FIG. 11. The left portion of the timing chart of FIG. 12 shows a normal state wherein the implantable electrode lead 10 operates normally, and the right portion of the timing chart of FIG. 12 shows an abnormal state wherein the low-resistant conductor wire 40 constituting the implantable electrode lead 10 is disconnected.

Referring to FIG. 11, the electrical resistance measurement circuit 60 surrounded by a broken line is built in the implantable heart pacemaker 8 as part of it, and the portion surrounded by a full line indicates a circuit that connects the implantable heart pacemaker 8 to a living tissue by using the implantable electrode lead 10, in the same manner as in FIG. 3 or 8.

More specifically, the implantable heart pacemaker 8 and implantable electrode lead 10 are connected to each other through the connector pin 1, connector ring 2, and connector cavity 9. As the power supply of the total electrical resistance measurement circuit 60, −2.8 [V] is supplied to a VSS 62 side with reference (0 V) to a COM 61.

The arrangement of the total electrical resistance measurement circuit 60 will be described first. An FET 51 is a switching transistor for outputting a pacing pulse. An OP 57 is an operational amplifier, and a COMP 63 is a comparator. An AND 70 is an AND circuit; an FF 67, a flip-flop circuit; and a C 58, a 10 μF output capacitor. R7 to R12 are resistors. The R7, R8, R9, R10, R11, and R12 respectively have resistances of 10 Ω, 1 MΩ, 1 MΩ, 490 kΩ, 10 kΩ, and 1 MΩ.

An example of electrical resistance measurement operation performed by the total electrical resistance measurement circuit 60 will be described.

[OP Output at Low PTRG Level: ISNS (0)]

A pacing trigger signal PTRG 52 to the FET 51 is normally at low level (VSS: −2.8 V), as shown in the normal state of FIG. 12, and changes to high level (VSS: 0 V) only when a pulse signal is input as shown in an interval between t1 and t2. When the PTRG 52 is at low level, the FET 51 is OFF. An after pulse signal AFT 55 is normally at high level (COM: 0 V). At this time, an FET 53 is OFF.

When the FETs 51 and 53 are OFF, only a current via COM 61→R8→point B 56→R9 flows to a point A 54, and a current via the FET 51 does not flow to it.

The R8 and R9 make up a bias circuit for setting the operating point of the point B 56 to be equal to a reference voltage AG of the OP amplifier 57, comparator 63, and the like. The reference voltage AG is set at the intermediate point of the power supply voltage, i.e., at VSS/2.

From R8, R9>>R7, the voltage drop across the R7 is approximately 0, and the potential at the point B 56 is VSS/2. Accordingly, the OP 57 output ISNS (0) at this time is as shown in equation (2):

$$ISNS(0)=VSS/2 \tag{2}$$

<OP Output at High PTRG Level: ISNS (I)>

Subsequently, when the pacing trigger signal PTRG 52 is input as the pulse signal (high level: 0 V) shown in the normal state of FIG. 12, the FET 51 is turned on, and a pacing pulse is generated between the connector ring 2 and connector pin 1 through the output capacitor C 58 (10 μF).

The voltage at this time, i.e., a pacing voltage Vp, sets the connector pin to −2.8 [V] with reference to the connector ring 2. The current flowing at this time, i.e., a pacing current Ip, flows via COM 61→connector ring 2→ring electrode 3→tip electrode 4→connector pin 1→C58→FET 51→R7 →VSS.

Therefore, with reference to VSS, the potential (point A 54) between the FET 51 and R7 is given by equation (3):

$$V(I)=Ip \cdot R7 \tag{3}$$

Also, as the current via R8 and R9 is sufficiently smaller than the pacing current Ip, the potential ISNS (I) at the connection point B 56 between R8 and R9 is given by equation (4):

$$ISNS(I)=(V(I)+VSS)/2 \tag{4}$$

Assuming that the gain of the OP 57 is G (=50 times), in accordance with equations (4) and (2), the pacing current Ip is obtained from equation (5):

$$V(ISNS) = G[ISNS(I) - ISNS(0)] \qquad (5)$$
$$= G \cdot V(I)/2 = G \cdot Ip \cdot R7/2$$

That is, the pacing current Ip is given by equation (6):

$$Ip = 2 \cdot V(ISNS)/(G \cdot R7) \qquad (6)$$

Hence, by using equation (6), a total electrical resistance ZL (=|Vp/Ip|) can be expressed by equation (7):

$$ZL = |Vp/Ip| \qquad (7)$$
$$= Vp \cdot G \cdot R7/(2 \cdot V(ISNS))$$

When Vp=−2.8 [V], R7=10 [Ω], and G=50 are substituted into equation (7), the total electrical resistance ZL can be obtained by equation (8):

$$ZL = 700/V(ISNS) \qquad (8)$$

<Measurement of Total Electrical Resistance: V (ISNS)>

Therefore, equation (8) shows that to detect disconnection of one low-resistant conductor wire 40 of the implantable electrode lead 10 by measuring the total electrical resistance is to measure a change in V (ISNS).

Strictly, during the pacing pulse period, the voltage gradually increases because, e.g., the pacing current charges the C 58. Therefore, if an output capacitor of about 10 µF is used as the output capacitor C 58 and measurement is performed at the initial stage of generation of the pacing pulse, an influence on the measurement value can be neglected.

After the pacing pulse ends, an AFT signal (not shown) changes to low level during a predetermined period of time (several 10 ms). The FET 53 is turned on, so that the charge accumulated in the C 58 is removed and the load state is restored to the initial state, thereby preparing for the next measurement.

<Disconnection Diagnosis Using V (ISNS)>

Disconnection diagnosis using V (ISNS) will be described. From equation (8), V (ISNS) can be obtained by equation (9):

$$V(ISNS) = 700/ZL \qquad (9)$$

From the calculation result of FIG. 10, if a total electrical resistance Z in the normal state, i.e., before disconnection, is 1,028 [Ω] and a total electrical resistance Z in the abnormal state, i.e., when one low-resistance conductor wire is disconnected, is 1,271 [Ω], then the outputs V (ISNS) 62 of the OP 57 before and after disconnection are as follows:

Output in Normal State: V (ISNS)=0.68 [V]
Output in Abnormal State: V (ISNS)=0.55 [V]

From the above result, an intermediate value of 0.61 [V] between the outputs in the normal and abnormal states is set as a comparison voltage VREF 65 (=0.61 [V]) used for determining presence/absence of disconnection by the COMP 63.

Assuming that a case wherein the input voltage to the COMP 63 satisfies the condition of V (ISNS)>VREF 65 is defined as a normal state and a case wherein the input voltage to the COMP 63 satisfies the condition of V (ISNS) ≦VREF 65 is defined as an abnormal state, the normal state and the abnormal state can be discriminated from each other by using the measurement value of V (ISNS).

How to discriminate disconnection with the V (ISNS) 62, COMP 63, VREF 64, AND 70, and FF 67 will be described in detail. In the time period between t1 and t2 in the timing chart of FIG. 12, a PTRG 52 signal is output, and the V (ISNS) 62 is measured.

The COMP 63 compares the input V (TSNS) 62 and the VREF 64. When a V (ISNS) signal satisfying V (ISNS) 62>VREF 64 and thus indicating a normal state is input, a low-level signal (−2.8 V) of the CMPOUT 69 of FIG. 12 that indicates the normal state is output during the time period between t1 and t2.

When a signal V (ISNS) satisfying V (ISNS) 62<VREF 64 and thus indicating an abnormal state is input, a high-level signal (0 V) of a CMPOUT 69 of FIG. 12 that indicates the abnormal state is output during the time period between t1 and t2.

Between t1 and t2, the AND 70 compares the two pulse signals, i.e., the input signal CMPOUT 69 and an MES 65. When the CMPOUT 69 is at low level and the MES 65 is at high level, a low-level (−2.8 V) signal is output as an ANDOUT 66, as shown in the normal state of FIG. 12. When the CMPOUT 69 is at high level and the MES 65 is at high level, a high-level (0 V) signal is output as the ANDOUT 66 during the time period between t1 and t2, as shown in the abnormal state of FIG. 12.

Between t1 and t2, the flip-flop FF 67 outputs a low-level (−2.8 V) signal as a FAIL 68 when the input signal ANDOUT 66 is at low level, as shown in the normal state of FIG. 12, and a high-level (0 V) signal as the FAIL 68 when the ANDOUT 66 is at high level, as shown in the abnormal state of FIG. 12.

Hence, the disconnection state of the implantable electrode lead 10 is checked by using the signal FAIL 68 shown in FIG. 12 and output from the flip-flop FF 67. When FAIL 68 is at high level, this state can be determined as the abnormal state (disconnection). When FAIL 68 is at low level, this state can be determined as the normal state.

[Resistance Measurement in Unipolar Mode]

The resistance measurement in the bipolar mode has been described. In a unipolar mode, the connector ring 2 and the R5 and R6 in FIG. 11 are omitted, and a heart pacemaker main body case replaces the ring electrode 3. Accordingly, it can readily be understood that resistance measurement in the unipolar mode can be performed by the same circuit system.

Measurement of the lead resistance need not always be performed upon output of a pacing pulse. More specifically, the voltage level that can pulsate the vital heart has a lower limit (pacing threshold). When the voltage level of the output pulse in lead resistance measurement is set to the lower limit or less, the lead resistance can be measured without accompanying pacing.

More specifically, referring to FIG. 11, this can be achieved by controlling the voltage level of the gate input signal PTRG to the FET 51 in an analog manner such that the output pulse from the drain of the FET 51 with respect to the lead resistance has a comparatively low voltage level (e.g., 0.1 (V)) (a conventional logic signal is separately input to the FET 67).

[Early Detection System for Disconnection]

Sometimes the bioelectrical resistance changes by as large as 500 [Ω] to 1,000 [Ω], during several days immediately after implantation of an implantable heart pacemaker, due to inflammation of the tissue. Even during a stable period at a lapse of one month or more after implantation, the bioelectrical resistance may fluctuate in a single day due to the influence of the motion of the body.

A system will be provided that can enable early detection for disconnection of a conductor without being influenced by fluctuation in lead electrical resistance caused by these physiological factors.

Figure 13:
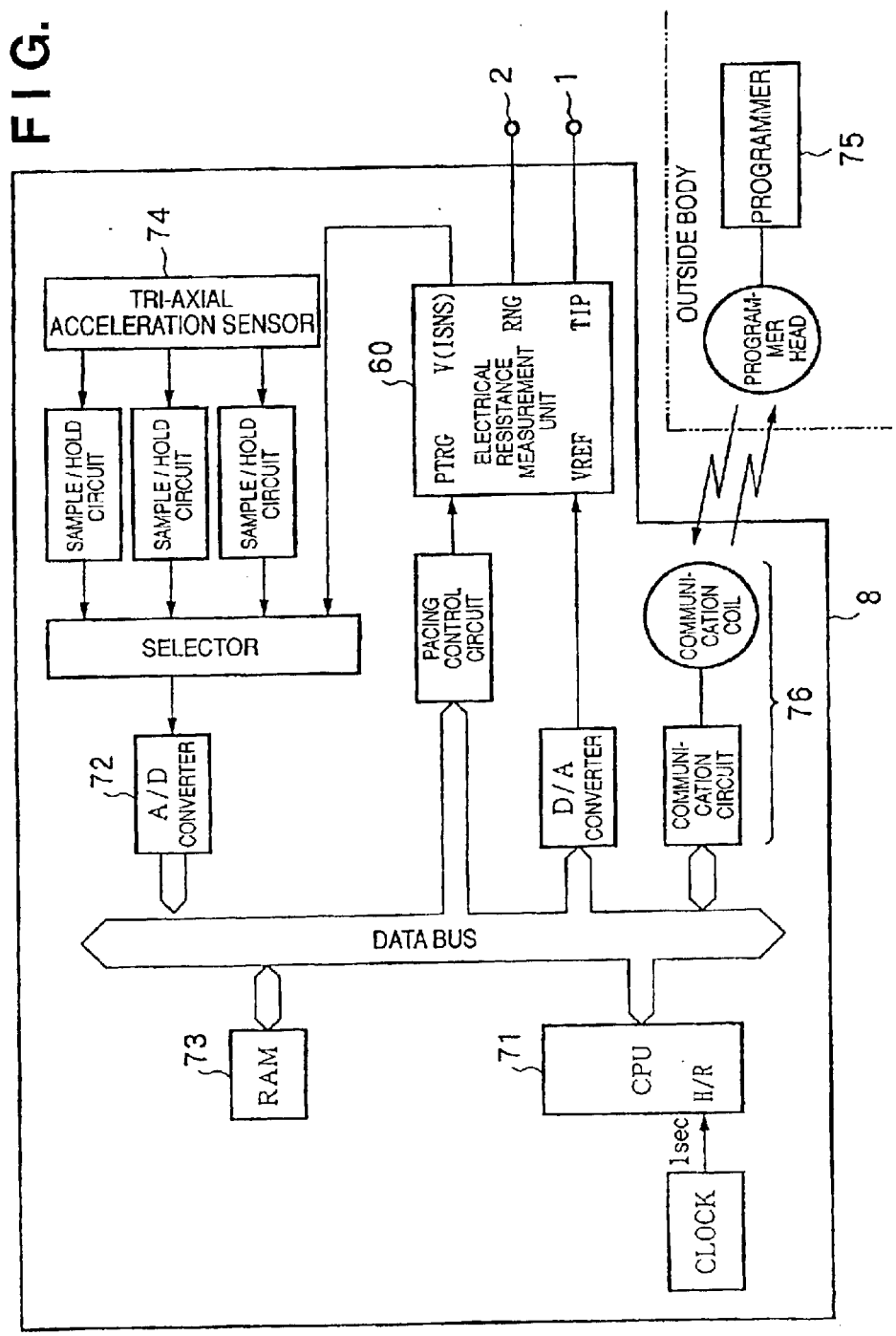
FIG. 13 shows a disconnection early detection system.
Figure 14:
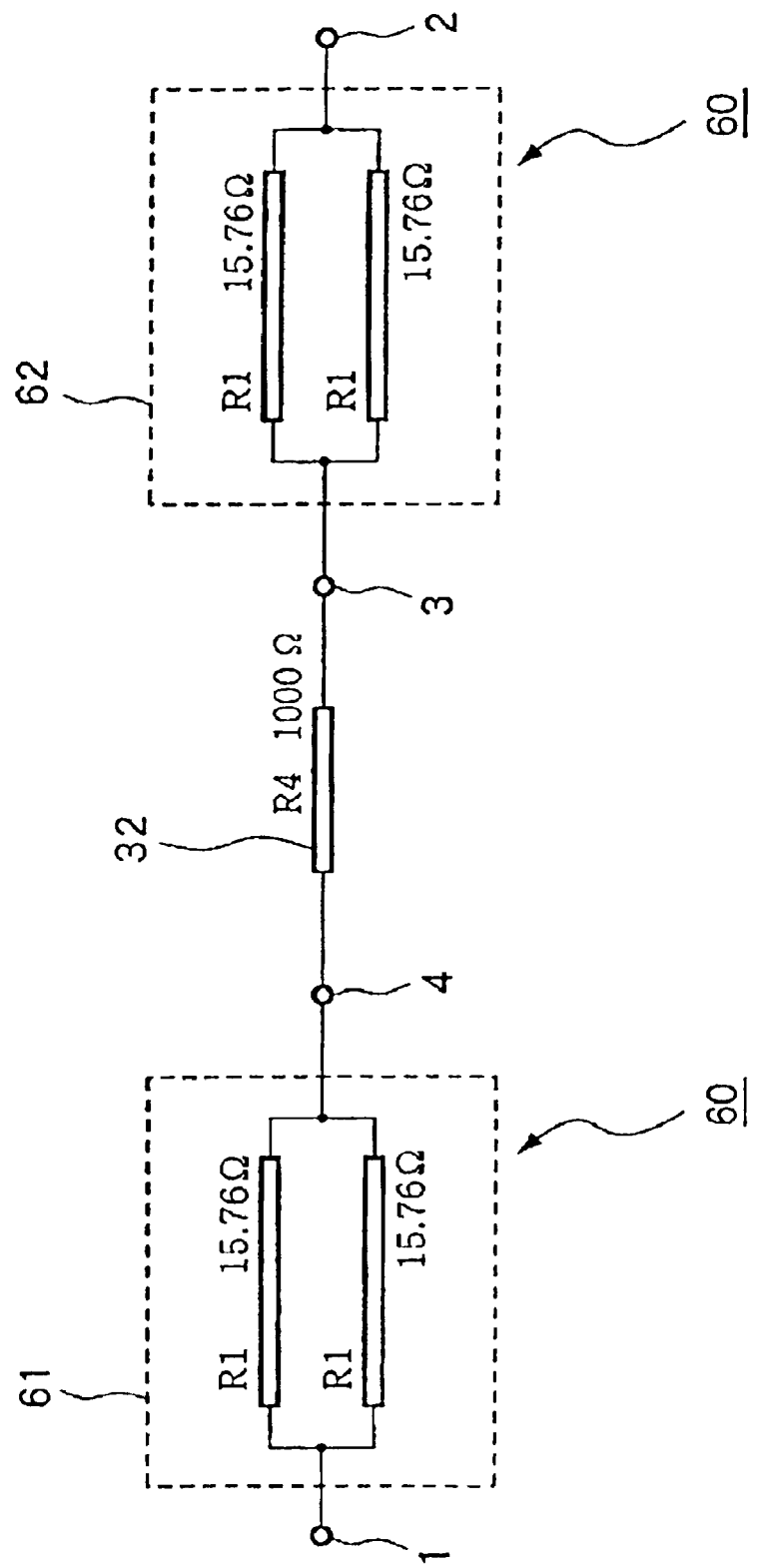
FIG. 14 is a circuit diagram obtained when a conventional implantable electrode lead is connected to the living body.

FIG. 13 is a block diagram showing an embodiment of this system. Referring to FIG. 13, an electrical resistance measurement unit 60 corresponds to the electrical resistance measurement circuit 60 of FIG. 11. An implantable electrode lead 11 is connected to the terminal of a connector ring 2 and the terminal of a connector pin 1.

In this embodiment, the electrical resistance between the terminals of the connector ring 2 and connector pin 1 is measured. If the implantable electrode lead is a unipolar lead, the electrical resistance between the terminal of the connector pin 1 and the casing of the heart pacemaker, i.e., a CASE terminal, is measured.

A V (ISNS) output from the electrical resistance measurement unit 60 is periodically A/D-converted by an A/D converter 72 under the control of a CPU 71, and is stored in a RAM 73. The implantable heart pacemaker 8 is provided with a tri-axial acceleration sensor 74 that can output a DC output. The tri-axial acceleration sensor 74 can detect not only the motion state but also the posture of the patient implanted with the heart pacemaker 8.

The sensor output is A/D-converted by the A/D converter 72 at a time point near electrical resistance measurement described above, and is stored in the RAM 73 for the respective components of the tri-axial acceleration while being time-related with the V (ISNS) 62. Data stored in the RAM 73 can be read out by a programmer 75 outside the living body by using a transmitting/receiving means 76 similar to that provided to a general heart pacemaker. When the V (ISNS) 62 read out by the programmer 75 and the sensor data are analyzed with a predetermined condition, whether an abnormality occurs in the implanted electrode lead can be detected at an early stage.

More specifically, attention is paid to, of the sensor outputs, a pattern obtained during rest, preferably one during sleeping, and the V (ISNS) 62 corresponding to this is used, so the total electrical resistance which is not influenced by the vital motion or position of the patient can be measured.

The pattern during sleeping can be easily discriminated because it has no AC component caused by body motion and, of the tri-axial acceleration components, its traveling-direction component is g (gravitational acceleration) and a component perpendicular to this is 0. If the programmer 75 performs a process in a software manner such as pattern matching to automatically detect this pattern from the sensor output data, and only the V (ISNS) 62 which is recorded when this pattern occurs is displayed on the programmer screen (not shown), the time of inspection required by the doctor may be further shortened.

Alternatively, this process may be performed in the heart pacemaker 8. More specifically, referring to FIG. 13, an output read out from the output from the tri-axial acceleration sensor 74 may be temporarily stored in a storage, and be subjected to pattern matching by the CPU 71. The V (ISNS) 62 may be recorded in the RAM 73 when the pattern matches a predetermined condition, e.g., the condition during sleeping described above. In this case, the sensor output need not always be recorded.

To relate the output from the measuring means and the detection result of the tri-axial acceleration sensor to each other in another manner, in place of the V (ISNS) 62, a comparison output FAIL in the electrical resistance measurement unit 60 described above may be stored in the RAM 73. In this case, easy-to-read display can be made, although it may not be quantitative.

In this embodiment, the tri-axial acceleration sensor 74 is used as a "sensor that can detect at least one of the moving state and position of the patient". Alternatively, a uni-axial acceleration sensor can detect the state of the patient to a certain degree.

The sensor need not be an acceleration sensor. Any sensor generally used in rate response control, e.g., a vibration sensor using a mercury ball or piezoelectric element, or a ventilation amount sensor employing chest electrical resistance measurement, can be used as the "sensor that can detect at least one of the moving state and position of the patient" of the present invention.

So far the embodiments of the present invention have been described in detail. Note that the scope of claims incorporates all the arrangements that can be chosen to obtain substantially the same effect as that described in the present specification.

INDUSTRIAL APPLICABILITY

As has been described above, in the implantable electrode lead with a bipolar type insulated parallel-wire coil structure according to the present invention, the electrical resistance can be kept low, and when one of a plurality of conductor wires arranged for one electrode is disconnected, a change in electrical resistance generated by disconnection can be detected without being influenced by a contact resistance, so that a symptom of disconnection of the implantable electrode lead can be informed at an early stage before complete disconnection. Also, an implantable medical instrument that can be used more safely can be provided by using the implantable electrode lead according to the present invention.

What is claimed is:

1. An implantable electrode lead having a distal end provided with at least one electrode to be implanted in a predetermined portion of a living body in order to perform at least one of transmission of an electrical stimulation pulse to a living body and sensing of an electrical signal from the living body, a proximal end provided with connecting means having at least one connecting terminal to be connected to an implantable medical instrument, and a lead body provided between said distal end and said proximal end and adapted to electrically connect said at least one electrode to said at least one connecting terminal, said lead body comprising a helical parallel coil of a plurality of conductive wires respectively having different properties and insulated from each other, wherein said helical parallel coil is made by rolling the plurality of conductive wires in parallel with the same diameter so that the plurality of conductive wires are next to each other, and said plurality of conductive wires electrically connecting said at least one electrode to said at least one connecting terminal in parallel so as to form a parallel circuit.

2. The implantable electrode lead according to claim 1, wherein said different properties include different electrical resistances and different mechanical properties.

3. The implantable electrode lead according to claim 1, wherein each of said plurality of conductive wires is a conductive wire with a single layer made of at least one metal material, or a composite conductive wire with a plurality of different single layers made of at least one metal material.

4. The implantable electrode lead according to claim 3, wherein said composite conductive wire with said plurality of different single layers has a clad structure obtained by covering a first single layer with a second single layer among said plurality of types of single layers.

5. The implantable electrode lead according to claim 3, wherein said composite conductive wire has a first single layer made of a metal material or alloy material with an electrical resistivity of not more than 5 $\mu\Omega$·cm and a second single layer made of a metal material or alloy material with an electrical resistivity of not less than 5 $\mu\Omega$·cm.

6. The implantable electrode lead according to claim 3, wherein said first and second single layers of said composite conductive wire contain silver and a cobalt alloy, respectively.

7. The implantable electrode lead according to claim 1, wherein said plurality of conductive wires are made of different materials.

8. The implantable electrode lead according to claim 1, wherein among said plurality of conductive wires, a first conductive wire has an electrical resistivity of not more than 5 $\mu\Omega$·cm and a second conductive wire has an electrical resistivity of not less than 5 $\mu\Omega$·cm.

9. An implantable medical instrument using an implantable electrode lead having at least one electrode to be implanted in a predetermined portion of a living body and a lead body to electrically connect said at least one electrode to at least one connecting terminal of said instrument, said lead body comprising a helical parallel coil of a plurality of conductive wires respectively having different properties and insulated from each other, wherein said helical parallel coil is made by rolling the plurality of conductive wires in parallel with the same diameter so that the plurality of conductive wires are next to each other, said plurality of conductive wires electrically connecting said at least one electrode to said at least one connecting terminal in parallel so as to form a parallel circuit, and said implantable medical instrument has informing means for determining that at least one of said plurality of conductive wires is damaged based on conductivity between said at least one electrode and said at least one connecting terminal, and for informing of the damage.

10. The implantable medical instrument according to claim 9, further having measuring means for measuring a motion state or posture of the living body where said electrode is implanted.

11. The implantable medical instrument according to claim 10, wherein said measuring means further has acceleration sensor means for measuring an acceleration, and measures the motion state or posture of the living body on the basis of a measurement result of said acceleration sensor means.

12. The implantable medical instrument according to claim 10, said implantable medical instrument further has storage means, and when a measurement result obtained by said measuring means satisfies a predetermined condition, the measurement result is recorded in said storage means.

13. The implantable medical instrument according to claim 9, wherein said informing means measures a parameter that changes on the basis of a change in total electrical resistance of said plurality of conductive wires, compares the parameter with a preset reference parameter, and informs that at least one of said plurality of conductive wires is fractured when the parameter that changes is smaller than the reference parameter.

14. The implantable medical instrument according to claim 13, wherein the parameter includes either one of current, frequency, and time.

15. The implantable medical instrument according to claim 9, wherein said different properties include different electrical resistances and different mechanical properties.

* * * * *